United States Patent [19]
Thompson et al.

[11] Patent Number: 5,646,336
[45] Date of Patent: Jul. 8, 1997

[54] ATOMIZING, CONTINUOUS, WATER MONITORING MODULE

[75] Inventors: Cyril V. Thompson, Knoxville; Marcus B. Wise, Kingston, both of Tenn.

[73] Assignee: Lockheed Martin Energy Systems, Inc., Oak Ridge, Tenn.

[21] Appl. No.: 644,887

[22] Filed: May 10, 1996

[51] Int. Cl.$^6$ .............. G01N 7/00; G01N 30/02; A62C 35/68

[52] U.S. Cl. .......... 73/61.43; 73/19.1; 73/53.01; 422/68.1

[58] Field of Search .............. 73/61.43, 19.1, 73/53.01; 422/68.1

[56] References Cited

U.S. PATENT DOCUMENTS

| | | | |
|---|---|---|---|
| 2,762,218 | 9/1956 | Ohlheiser | 73/53 |
| 3,077,105 | 2/1963 | Ohlheiser | 73/53 |
| 3,367,850 | 2/1968 | Johnson | 204/1 |
| 3,477,279 | 11/1969 | Perlaky | 73/61.1 |
| 4,340,391 | 7/1982 | Demaison et al. | 23/230 EP |
| 5,076,097 | 12/1991 | Zarrin et al. | 73/61.1 |
| 5,222,032 | 6/1993 | Fleming | 364/502 |
| 5,258,057 | 11/1993 | Baykut | 95/89 |
| 5,266,496 | 11/1993 | Dacruz | 436/157 |
| 5,476,637 | 12/1995 | Fuhrmann | 422/68.1 |
| 5,495,893 | 3/1996 | Roberts et al. | 169/37 |

*Primary Examiner*—Hezron E. Williams
*Assistant Examiner*—J. David Wiggins
*Attorney, Agent, or Firm*—Ivan L. Ericson

[57] ABSTRACT

A system for continuously analyzing volatile constituents of a liquid is described. The system contains a pump for continuously pumping the liquid to be tested at a predetermined flow rate into an extracting container through a liquid directing tube having an orifice at one end and positioned to direct the liquid into the extracting container at a flow rate sufficient to atomize the liquid within the extracting container. A continuous supply of helium carrier gas at a predetermined flow rate is directed through a tube into the extracting container and co-mingled with the atomized liquid to extract the volatile constituents contained within the atomized liquid. The helium containing the extracted volatile constituents flows out of the extracting container into a mass spectrometer for an analysis of the volatile constituents of the liquid.

11 Claims, 2 Drawing Sheets

ATOMIZING, CONTINUOUS, WATER MONITORING MODULE

This invention was made with Government support under contract DE-AC05-84OR21400 awarded by the U.S. Department of Energy to Lockheed Martin Energy Systems, Inc. and the Government has certain rights in this Invention.

FIELD OF THE INVENTION

The present invention relates to a water monitoring module, more particularly, to a atomizing, continuous, water monitoring module.

BACKGROUND OF THE INVENTION

The standard method for analysis of volatile organic compounds in water has been purge and trap, in which a water sample, typically 40 ml, is purged with a gas stream for a period of time and the volatile organic compounds which are partitioned into the gas stream are then trapped on a sorbent cartridge and analyzed by thermal desorption gas chromatograph/mass spectrometer. This means that grab samples had to be acquired and analyzed from water wells, surface water, process streams, etc. If a treatment process had to be characterized over a period of time, only a finite number of samples could be acquired for this purpose. Two spray and trap methods for water analysis utilizing a spray nozzle that volatilized aqueous organics for adsorption on a trap prior to analysis were discussed in recent publications. (Gerhard Matz and Peter Kesners, "Spray and Trap Method for Water Analysis by Thermal Desorption Gas Chromatography/Mass Spectrometry in Field Applications", Anal. Chem., 1993, 65, 2366–2371 and Gokkhan Baykut and Annette Voigt, "Spray Extradion of Volatile Organic Compounds from Aqueous Systems into the Gas Phase for Gas Chromatography/Mass Spectrometry", Anal. Chem. 1992, 64, 677–681). Another publication discussed an on line monitoring of volatiles in aqueous solutions using membrane introduction mass spectrometry. (Scott J. Bauer and R. Graham Cooks, "MIMS for trace-level determination of organic analytes in on-line process monitoring and environmental analysis", American Laboratory, October 1993, pp. 36, 38–43, 45–48, 51, 52). However, the membrane introduction mass spectrometry is not applicable to larger or more polar compounds.

U.S. Pat. No. 5,272,337 to Thompson et al. describes a mass spectrometer sample introduction system for introducing gaseous samples from a wide range of environmental matrices into a mass spectrometer for analysis of the samples. A water purge sample module uses a vial containing water containing volatile compounds and a high speed needle sparge purging system for extracting the volatile compounds from the water for analysis in the mass spectrometer. This method requires obtaining separate samples in a vial and analyzing the volatile compounds extracted from the water one at a time.

Other methods such as IR have been used but are not as sensitive or specific in their identification of compounds of interest. The present invention fulfills the need for a continuous analysis in real-time of volatile organic compounds in water samples or process streams with detection limits in the low ppb range.

OBJECTS OF THE INVENTION

Accordingly, it is an object of the present invention to provide an atomizing, continuous, water monitoring module.

Further and other objects of the present invention will become apparent from the description contained herein.

SUMMARY OF THE INVENTION

In accordance with one aspect of the present invention, a new and improved system for continuously analyzing volatile components of a liquid comprises an extraction means for continuously extracting the volatile components contained in a liquid from the liquid, a liquid displacing means for continuously displacing the liquid at a predetermined flow rate, a carrier gas supply means for continuously supplying a carrier gas and a gas analyzing means for continuously analyzing the volatile components of the liquid. The liquid displacing means has an inlet port and an outlet port. The gas analyzing means has a sample gas inlet port. The extraction means comprises a closed container, a carrier gas directing means and a liquid directing means. The closed container has an inside wall, a liquid inlet port, a liquid outlet port, a carrier gas inlet port and a sample gas outlet port. The liquid displacing means has a liquid inlet port and a liquid outlet port. The liquid outlet port of the liquid displacing means is in fluid communication with the liquid inlet port of the closed container of the extraction means. The carrier gas supply is in fluid communication with the carrier gas inlet port of the closed container of the extracting means. The carrier gas directing means has a carrier gas inlet port and a carrier gas outlet port. The carrier gas inlet port of the carrier gas directing means is in fluid communication with the carrier gas inlet port of the closed container of the extraction means. The sample gas outlet port of the closed container of the extraction means is in communication with the sample gas inlet port of the gas analyzing means. The liquid directing means has a liquid inlet port and a liquid outlet port. The liquid inlet port of the liquid directing means is in fluid communication with the liquid inlet port of the closed container of the extraction means. The liquid outlet port of the liquid directing means contained within the closed container of the extraction means is positioned for directing the liquid against the inside wall of the closed container of the extraction means.

In accordance with another aspect of the present invention, a new and improved method for continuously analyzing volatile components contained in a liquid comprises the following steps;

Step 1. A system is provided for continuously analyzing volatile components of a liquid. The system comprises: an extraction means for continuously extracting the volatile components contained in the liquid from the liquid, a liquid displacing means for continuously displacing the liquid at a predetermined flow rate, a carrier gas supply means for continuously supplying a carrier gas and a gas analyzing means for continuously analyzing the volatile components of the liquid. The liquid displacing means has an inlet port and an outlet port. The gas analyzing means has a sample gas inlet port. The extraction means comprises closed container, a carrier gas directing means and a liquid directing means. The closed container has an inside wall, a liquid inlet port, a liquid outlet port, a carrier gas inlet port and a sample gas outlet port. The liquid displacing means has a liquid inlet port and a liquid outlet port. The liquid outlet port of the liquid displacing means is in fluid communication with the liquid inlet port of the closed container of the extraction means. The carrier gas supply is in communication with the carrier gas inlet port of the closed container of the extracting means. The carrier gas directing means has a carrier gas inlet port and a carrier gas outlet port. The carrier gas inlet port of carrier gas directing means is in fluid communication with the carrier gas inlet port of the closed container of the extraction means. The sample gas outlet port of the closed container of the extraction means is in communication with the sample gas inlet port of the gas analyzing means. The liquid directing means has a liquid inlet port and a liquid outlet port. The liquid inlet port of the liquid directing means is in fluid communication with the liquid inlet port of the closed container of the extraction means. The liquid outlet port of the liquid directing means contained within the closed container of the extraction means is positioned for directing the liquid against the inside wall of the closed container of the extraction means.

Step 2. The liquid inlet port of the liquid displacing means is placed in a liquid to be tested.

Step 3. The liquid is continuously displaced through the liquid displacing means at a predetermined flow rate into the liquid directing means contained in the closed container of the extraction means. The predetermined flow rate is sufficient to direct the liquid from the outlet port of the liquid directing means against the inside wall of the closed container at a force sufficient to atomize the liquid within the closed container forming an atomized liquid.

Step 4. A carrier gas is continuously provided from the carrier gas supply into the closed container of the extraction means through the carrier gas directing means at a flow rate sufficient to co-mingle with the atomized liquid sufficient to extract the volatile components contained in the liquid from the atomized liquid to form a sample gas and to exit the sample gas from the closed container through the sample gas outlet port of the closed container into the sample gas inlet port of the gas analyzing means.

Step 5. The volatile components in the sample gas are continuously analyzed with the analyzing means. sample gas from the closed contained through the sample gas outlet port of the closed container into the sample gas inlet port of the gas analyzing means.

Step 5. The volatile components in the sample gas are continuously analyzed with the analyzing means.

For a better understanding of the present invention, together with other and further objects, advantages and capabilities thereof, reference is made to the following disclosure and appended claims in connection with the above described drawings.

DETAILED DESCRIPTION OF THE PREFERRED EMBODIMENTS

The present invention provides for the immediate quantitation of volatile organic compounds in water. It also provides for the real-time monitoring of such compounds in water samples or process streams. Variations in the concentrations of these compounds can be detected and plotted in real-time. The present invention has been used successfully to monitor the volatiles levels in seep water as a water supply was being treated. The concentrations of a number of volatile organic compounds, such as toluene, benzene, methyl ethyl ketone, TCA, DCA, xylenes, ethylbenzene and C2-Benzenes, were continuously followed during the treatment process for destroying the compounds.

One advantage of the present invention is that no water samples need be transferred, treated and then disposed of, especially if the samples are classified as a hazardous waste, a significant benefit over other methods of water analysis.

Figure 1:
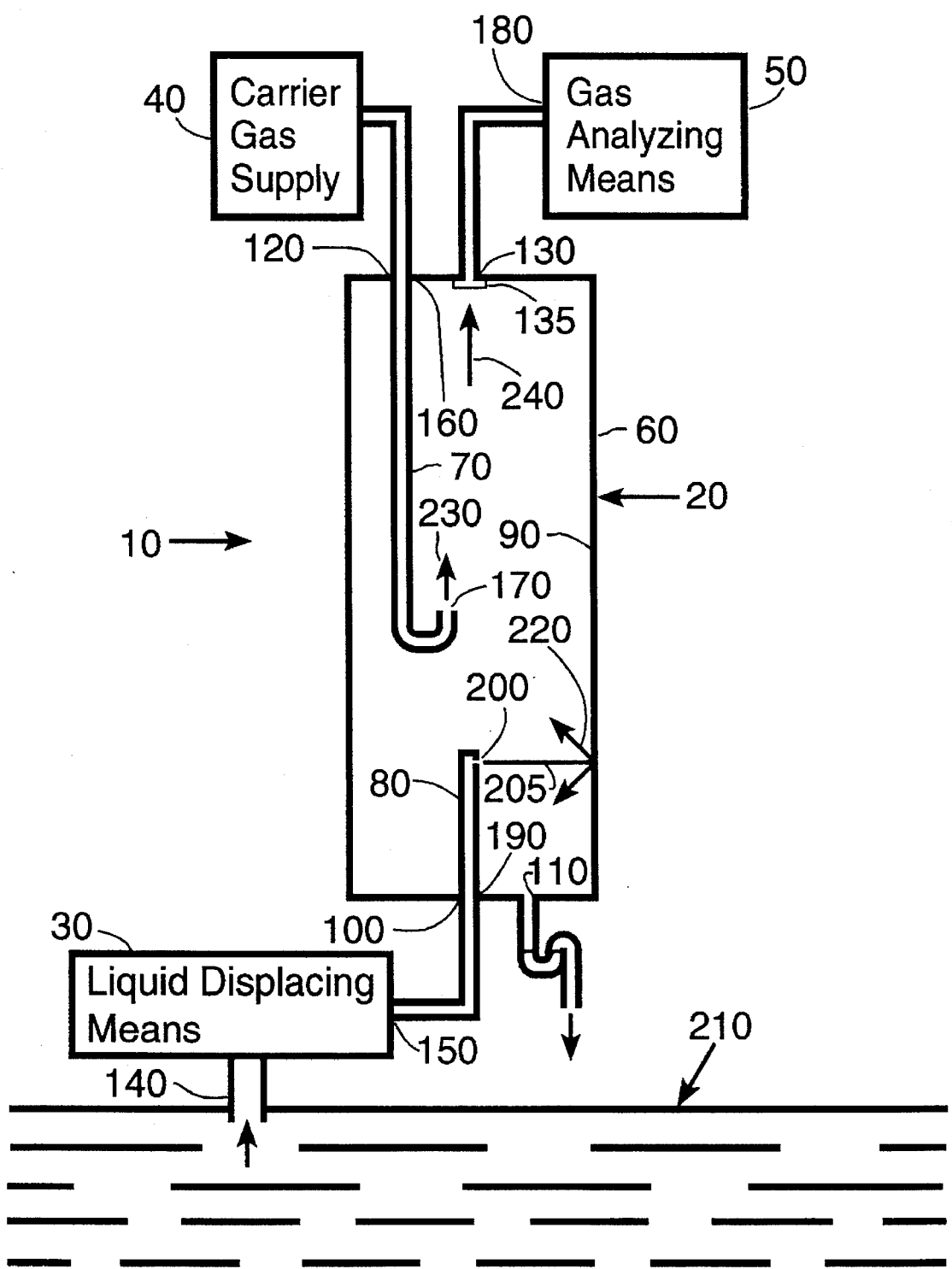
FIG. 1 is a cross-sectional view of a system for continuously analyzing volatile components of a liquid in accordance with the present invention.
Figure 2:
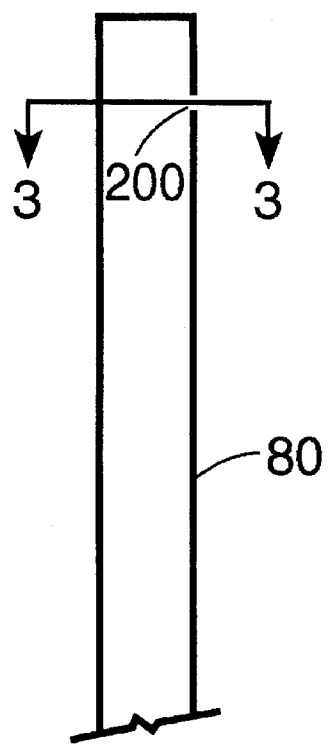
FIG. 2 is cross-sectional view of liquid directing means 80 of FIG. 1.
Figure 3:
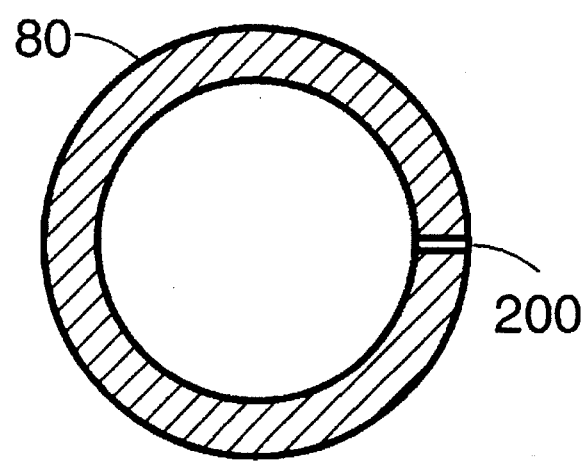
FIG. 3 is a cross-sectional top view along line 3—3 of FIG. 2 in accordance with the present invention.

Shown in FIG. 1 is system 10 which comprises extraction means 20 for continuously extracting volatiles from liquid 210, such as water, liquid displacing means 30, such as a pump, for continuously displacing liquid 210 into extraction means 20 at a predetermined flow rate, carrier gas supply 40, such as a pressurized gas cylinder of helium having a pressure regulator and a flow meter attached thereto, for continuously supplying carrier gas and gas analyzing means 50, such as a mass spectrometer as described in U.S. Pat. No. 5,272,337 to Thompson et al incorporated herein by reference thereto, for continuously analyzing the volatile components of liquid 210. Extraction means 20 comprises closed container 60, carrier gas directing means 70 and liquid directing means 80, such as a tube closed at one end and having a hole or holes in the walls of the tube. Closed container 60 has inside wall 90, liquid inlet port 100, liquid outlet port 110, carrier gas inlet port 120 and sample gas outlet port 130. FIG. 2 is a cross-sectional view of liquid directing means 80 showing liquid outlet port 200. FIG. 3 is a cross-sectional top view along line 3—3 of FIG. 2 of liquid directing means 80 showing liquid outlet port 200 having a diameter from about 0.005 to about 0.007 inches positioned to provide stream 205 of liquid 210, shown in FIG. 1, from liquid directing means 80 to inside wall 90 of closed container 60. Sample gas outlet port 130 of closed container 60 has liquid condensing means 135, such as a porous screen covering sample gas outlet port 130. Liquid displacing means 30 has liquid inlet port 140 and liquid outlet port 150. Liquid outlet port 150 of liquid displacing means 30 is in communication with liquid inlet port 100 of closed container 60. Carrier gas supply 40 is in communication with carrier gas inlet port 120 of closed container 60. Carrier gas directing means 70 has a carrier gas inlet port 160 and carrier gas outlet port 170. Carrier gas inlet port 160 of carrier gas directing means 70 is in communication with carrier gas inlet port 120 of closed container 60. Sample gas outlet port 130 of closed container 60 is in communication with sample gas inlet port 180 of gas analyzing means 50. Liquid directing means 80 has a liquid inlet port 190 and liquid outlet port 200. Liquid inlet port 190 of liquid directing means 80 is in communication with liquid inlet port 100 of closed container 60. Liquid outlet port 200 of liquid directing means 80 contained within closed container 60 is positioned for directing liquid 210 against inside wall 90 of closed container 60.

A method for continuously analyzing the volatile components contained in liquid 210, such as water, utilizing system 10 comprises the following: System 10 is provided. Liquid inlet port 140 of liquid displacing means 30 is placed in liquid 210 to be tested. Liquid 210 is continuously displaced through liquid displacing means 30 at a predetermined flow rate into liquid directing means 80 contained in closed container 60 of extraction means 20. The predetermined flow rate is sufficient to direct liquid 210 from liquid outlet port 200 of liquid directing means 80 against inside wall 90 of closed container 60 at a force sufficient to atomize liquid 210 within closed container 60 to form atomized liquid 220. Carrier gas 230, such as helium, is continuously provided from carrier gas supply 40 into closed container 60 through carrier gas directing means 70 at a flow rate sufficient to co-mingle with atomized liquid 220 sufficient to extract the volatiles contained in liquid 210 from atomized liquid 220 to form sample gas 240 and to exit sample gas 240 from closed container 60 through sample gas outlet port 130 of closed container 60 into sample gas inlet port 180 of gas analyzing means 50. The continuous flow of sample gas 240 comprising carrier gas 230 containing extracted volatiles from atomized liquid 220 into gas analyzing means 50 is continuously analyzed for the volatiles contained in carrier gas 230 with gas analyzing means 50.

A test was run comparing the efficiency using system 10 shown in FIG. 1 of the present invention with the efficiency of extracting volatiles, such as chlorine, from tap water by purging a vial containing tap water with a bubble purge of helium carrier gas and analyzing the helium carrier gas containing extracted volatiles from the tap water in a mass spectrometer system. The same tap water was used in the comparison and the same mass spectrometer system was used as depicted in U.S. Pat. No. 5,272,337 to Thompson et al. Incorporated herein by reference thereto. The volatile extraction efficiency of the atomizing procedure utilizing system 10 of the present invention was three times better than the volatile extraction efficiency of purging procedure utilizing the bubble purging of a vial of tap water with a helium carrier gas to extract the volatiles in the tap water. The pump used for the liquid displacing means 30 of system 10 for continuously analyzing volatile components of a liquid was a Xolox Corporation, Fort Wayne, Indiana, gear pump, model number 1261. The normal low pressure performance of this pump at 12V is 486 ml/min (7.67 GPH). The pressure rating of the exit port is 125 psig max. The inlet port of the pump is connected to an inlet strainer of 80 mesh maximum—(mesh size—0.007'maximum or 178 microns). The liquid outlet port 200 of liquid directing means 80 shown in FIG. I is a hole drilled perpendicularly into the side of liquid directing means 80. The hole diameter was 0.007 inches.

Alternative uses of the present invention include in situ sampling of ground water in wells and continuous monitoring of process or waste streams in industrial plants, hazardous waste site characterizations and for site remediations.

While there has been shown and described what is at present considered the preferred embodiments of the invention, it will be obvious to those skilled in the art that various changes and modifications may be made therein without departing from the scope of the invention as defined by the appended claims.

We claim:

1. A system for continuously analyzing volatile components of a liquid comprising:

an extraction means for continuously extracting volatile components contained in a liquid from said liquid; a liquid displacing means for continuously displacing said liquid at a predetermined flow rate, said liquid displacing means having an inlet port and an outlet port; a carrier gas supply means for continuously supplying a carrier gas and a gas analyzing means for continuously analyzing said volatile components of said liquid, said gas analyzing means having a sample gas inlet port; said extraction means comprising a closed container, a carrier gas directing means and a liquid directing means, said closed container having an inside wall, a liquid inlet port, a liquid outlet port, a carrier gas inlet port and a sample gas outlet port, said liquid displacing means having a liquid inlet port and a liquid outlet port, said liquid outlet port of said liquid displacing means being in fluid communication with said liquid inlet port of said closed container of said extraction means, said carrier gas supply being in fluid communication with said carrier gas inlet port of said closed container of said extracting means, said carrier gas directing means having a carrier gas inlet port and a carrier gas outlet port, said carrier gas inlet port of said carrier gas directing means being in fluid communication with said carrier gas inlet port of said closed container of said extraction means, said sample gas outlet port of said closed container of said extraction means being in fluid communication with said sample gas inlet port of said gas analyzing means, said liquid directing means having a liquid inlet port and a liquid outlet port, said liquid inlet port of said liquid directing means being in fluid communication with said liquid inlet port of said closed container of said extraction means, said liquid outlet port of said liquid directing means contained within said closed container of said extraction means being positioned for directing said liquid against said inside wall of said closed container of said extraction means, said liquid directing means being a tube closed at one end and said tube having a small through-put hole drilled perpendicular into said tube to form a liquid exit orifice for directing said liquid against said inside wall of said closed container at a force sufficient to atomize said liquid into a liquid gas aerosol.

2. A system for continuously analyzing volatile constituents of a liquid in accordance with claim 1 wherein said liquid displacing means is a pump.

3. A system for continuously analyzing volatile constituents of a liquid in accordance with claim 1 wherein said gas analyzing means is a mass spectrometer.

4. A system for continuously analyzing volatile constituents of a liquid in accordance with claim 1 wherein said liquid outlet port of said liquid directing means is a hole having a diameter from about 0.005' to about 0.007'.

5. A system for continuously analyzing volatile constituents of a liquid in accordance with claim 1 wherein said carrier gas supply means is a pressurized gas cylinder of helium having a pressure regulator and a flow meter attached thereto.

6. A system for continuously analyzing volatile constituents of a liquid in accordance with claim 1 wherein said sample gas outlet port of said closed container has a porous screen enclosure covering said outlet port to promote liquid condensation of the liquid in said sample gas passing through said sample gas outlet port.

7. A method for continuously analyzing volatile components contained in a liquid comprising the following steps;

Step 1. providing a system for continuously analyzing volatile components of a liquid, said system comprising: an extraction means for continuously extracting said volatile components contained in said liquid from said liquid; a liquid displacing means for continuously displacing said liquid at a predetermined flow rate, said liquid displacing means having an inlet port and an outlet port; a carrier gas supply means for continuously supplying a carrier gas and a gas analyzing means for continuously analyzing said volatile components of said liquid, said gas analyzing means having a sample gas inlet port; said extraction means comprising a closed container, a carrier gas directing means and a liquid directing means; said closed container having an inside wall, a liquid inlet port, a liquid outlet port, a carrier gas inlet port and a sample gas outlet port; said liquid displacing means having a liquid inlet port and a liquid outlet port; said liquid outlet port of said liquid displacing means being in fluid communication with said liquid inlet port of said closed container of said extraction means; said carrier gas supply being in fluid communication with said carrier gas inlet port of said closed container of said extracting means; said carrier gas directing means having a carrier gas inlet port and a carrier gas outlet port; said carrier gas inlet port of said carrier gas directing means being in fluid communication with said carrier gas inlet port of said closed container of said extraction means; said sample gas outlet port of said closed container of said extraction means being in fluid communication with said sample gas inlet port of said gas analyzing means; said liquid directing means having a liquid inlet port and a liquid outlet port; said liquid inlet port of said liquid directing means being in fluid communication with said liquid inlet port of said closed container of said extraction means; said liquid outlet port of said liquid directing means contained within said closed container of said extraction means being positioned for directing said liquid against said inside wall of said closed container of said extraction means, said liquid directing means being a tube closed at one end and said tube having a small through-put hole drilled perpendicular into said tube;

Step 2. placing said liquid inlet port of said liquid displacing means in said liquid to be tested;

Step 3. continuously displacing said liquid through said liquid displacing means at a predetermined flow rate into said liquid directing means contained in said closed container of said extraction means, said predetermined flow rate being sufficient to direct said liquid from said outlet port of said liquid directing means against said inside wall of said closed container at a force sufficient to atomize said liquid within said closed container forming an atomized liquid;

Step 4. continuously providing a carrier gas from said carrier gas supply into said closed container of said extraction means through said carrier gas directing means at a flow rate sufficient to co-mingle with said atomized liquid sufficient to extract said volatile components contained in said liquid from said atomized liquid to form a sample gas and to exit said sample gas from said closed container through said sample gas outlet port of said closed container into said sample gas inlet port of said gas analyzing means; and Step 5. Continuously analyzing said volatile components in said sample gas with said analyzing means.

8. A method for continuously analyzing volatile constituents of a liquid in accordance with claim 7 wherein said liquid displacing means is a pump.

9. A method for continuously analyzing volatile constituents of a liquid in accordance with claim 7 wherein said gas analyzing means is a mass spectrometer.

10. A method for continuously analyzing volatile constituents of a liquid in accordance with claim 7 wherein said liquid directing means is a spray nozzle.

11. A method for continuously analyzing volatile constituents of a liquid in accordance with claim 7 wherein said carrier gas supply means is a pressurized gas cylinder of helium having a pressure regulator and a flow meter attached thereto.

* * * * *